(12) United States Patent
Farb

(10) Patent No.: US 6,379,007 B1
(45) Date of Patent: Apr. 30, 2002

(54) EYE CHART WITH DISTINCT SYMBOLS AND METHODS FOR VISION TESTING

(76) Inventor: Mark Daniel Farb, 343 N. Mansfield Ave., Los Angeles, CA (US) 90036

( * ) Notice: Subject to any disclaimer, the term of this patent is extended or adjusted under 35 U.S.C. 154(b) by 0 days.

(21) Appl. No.: 09/694,801

(22) Filed: Oct. 23, 2000

(51) Int. Cl.$^7$ ................................................ A61B 3/02
(52) U.S. Cl. ..................................................... 351/239
(58) Field of Search ............................... 351/237, 238, 351/239, 240, 242, 243; 345/156, 22, 23, 25

(56) References Cited

U.S. PATENT DOCUMENTS

| | | | | |
|---|---|---|---|---|
| 4,611,893 A | * | 9/1986 | Schrier | 351/239 |
| 5,436,681 A | * | 7/1995 | Michaels | 351/240 |
| 5,844,544 A | * | 12/1998 | Kahn et al. | 345/156 |

OTHER PUBLICATIONS

*Duane's Ophthalmology On CD–ROM*, vol. 1, Chapter 10, "Clinical Ophthalmology," vol. 1, Chapter 33, "The Human Eye As An Optical System," vol. 2, Chapter 19, "Color Vision," edited by Tasman and Jaeger, published by Lippincott–Raven, 1997 edition, (five pages).
Wilson Ophthalmic Corp., "The Source," 1999 Catalog, cover sheet and pp. 40–45.
Graham–Field, "Illiterate Chart for 10 Feet," No. 2867–1262–1 (two pages).
Graham–Field, "Eye Test Chart for 10 Feet," No. 2867–1264 (one page).
J. G. Rosenbaum, M.D., "Rosenbaum Pocket Vision Screener" (one page).

* cited by examiner

*Primary Examiner*—George Manuel
(74) *Attorney, Agent, or Firm*—Christie, Parker & Hale, LLP

(57) ABSTRACT

An eye chart of the present invention has a plurality of symbols selected from a set of distinct symbols. The symbols in the set consist of numerals of 3, 4, 6, 7, and 9 and letters of A, E, F, H, J, K, L, P, T, X, and Y. In one embodiment, the symbols in the set further include a pictorial object. A method for vision testing of the present invention includes recording a value associated with an accuracy of identification of at least two of the letter, the numeral, and the pictorial objects on an eye chart by a person, and comparing the values for each eye of the patient. Because these symbols are distinct, the value recorded for visual acuity is accurate and consistent with each recordation. Further, the values are able to be used as aids in testing for neurological disorders or diseases. In another embodiment, the eye chart has symbols of red colors and of black colors. In another embodiment, the eye chart has variously colored symbols on colored backgrounds. Accuracy of identification of these colored symbols is recorded, compared, and used as an aid in diagnosing loss of color vision.

24 Claims, 3 Drawing Sheets

(2 of 3 Drawing Sheet(s) Filed in Color)

EYE CHART WITH DISTINCT SYMBOLS AND METHODS FOR VISION TESTING

FIELD OF THE INVENTION

The present invention is directed to an eye chart with distinct symbols. In particular, the eye chart has lines of symbols, where the symbols are selected from a set of distinct symbols. The symbols include at least one of letters, numerals and pictorial objects. In one embodiment, a first subset of symbols has a first color and a second subset has a second color. The eye chart permits consistent quantification of visual acuity, which aids in testing, diagnosing, and monitoring of neurological and ophthalmological diseases, loss of color vision, and retinal dystrophies, as well as monitoring of effectiveness and dosage of some drugs.

BACKGROUND OF THE INVENTION

A Snellen test is typically used to determine visual acuity. The Snellen test has a patient identify black block letters of the alphabet from an eye chart at a specified distance away from a Snellen chart. Typically, a doctor records the value associated with the line on the Snellen chart that the patient reads completely, e.g., 20/20. If the patient misses some letters on the 20/20 line, the doctor would write down "20/20–" for 20/20 minus. Some doctors use a Jaeger card to test a patient's visual acuity. The values of visual acuity for Jaeger are noted as, for example, J2, J4, and J6.

Snellen devised the familiar eye chart by defining a person with normal visual acuity as having a threshold visual angle of 1 minute of arc for black objects on a white background. One with normal visual acuity has 20/20 (6/6) vision. 20/20 (6/6) vision means the person has read a letter at 20 feet (6 meters) that was designed to be read at 20 feet (6 meters).

Accuracy of identification of the letters in the Snellen chart is based upon experience of the user with the chart and in reading the letters, familiarity with the letters, and psychological factors. Further, accuracy depends upon whether the chart letters are equally legible or whether some blur interpretation may be characteristic of the configuration of some of the letters. For example, as compared with the letter C, G is more difficult to identify and L is easier to identify.

Typically, the details of the symbols blur as the distance from the eye increases (or as the font decreases) and identification becomes more difficult. Some clinicians recognize that some symbols are similarly formed and, at a distance, look strikingly similar. As a result, the clinicians will sometimes credit the person taking the vision test with accurately identifying the strikingly similar symbol, and other times clinicians only give credit for identifying the exact symbol accurately. This type of subjective judgment leads to inconsistent quantification of vision acuity.

Visual acuity testing for illiterate persons, including children, typically utilizes designated illiterate charts having lines with symbols. These charts typically have symbols of a "Tumbling" E, wherein the person identifies with fingers the direction of the E. Other charts used to test visual acuity for illiterates include pictorial objects that are identified, and an HOTV chart for an HOTV test. In the HOTV test, the person matches each test letter to one of the four letters H, O, T, or V printed on a card that can be held in the person's hands.

Typically, a patient is tested for color blindness using Ishihara plates. Ishihara plates have colored dotted symbols on a colored dotted background. Typically, the red-green pattern of loss is most common.

Lesions of the inferior occipital cortex, neurological diseases, strokes, Multiple Sclerosis, and other disorders typically affect and disrupt color perception. The disruption in color perception results in reduced vividness of saturated or pure colors, particularly red. Testing of red desaturation is most often performed clinically by estimating the degree of desaturation by having the patient view a red object such as the red cap of a bottle of eye drops.

SUMMARY OF THE INVENTION

An eye chart of the present invention has a plurality of lines, each line with a plurality of symbols chosen from a set of symbols. The symbols in the set include letters and numerals, wherein each symbol in the set is substantially equal in size and distinguishing features. In one embodiment, the symbols in the set further include a pictorial object. The pictorial objects have non-confusing, distinct shapes.

A method for vision testing of the present invention includes recording values associated with an accuracy of identification of a letter and of a numeral on an eye chart by a patient, and comparing the two values for each eye of the patient. In one embodiment, the method further records a value associated with an accuracy of identification of the pictorial object on the eye chart, and compares the value associated with the accuracy of identification of the pictorial object with that of the letter and numeral.

In another embodiment, the method further records a value associated with an accuracy of identification of a first and a second set of symbols on the eye chart, and compares the two values. The first set of symbols is in a first color and the second set of symbols is in a second color. In one embodiment, the chart enables evaluation of subtle loss of color perception and the change over time.

In one embodiment, the numerals in the set of symbols consist of 3, 4, 6, 7, and 9. In another embodiment, the letters in the set of symbols consist of A, E, F, H, J, K, L, P, T, X, and Y. Letters and numbers that tend to be confused with each other are excluded. The letters may also be distinct characters of an alphabet other than the Latin alphabet. In one embodiment, at least one of the symbols is black, and at least another of the symbols is one of red and green.

Because of the distinct symbols, the eye chart permits doctors to render substantially consistent quantification of neurological abilities and changes therein. The methods of quantification of visual acuity permits testing or monitoring of loss of color vision, neurological diseases, drug treatments or retinal dystrophies by comparing the visual acuity for colored symbols to that of black symbols. Further, by comparing the visual acuity for letters and numerals, neurological diseases may be diagnosed and monitored.

Many of the attendant features of this invention will be more readily appreciated as the same becomes better understood by reference to the following detailed description and considered in connection with the accompanying drawings in which like reference symbols designate like parts throughout.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

Figure 1:
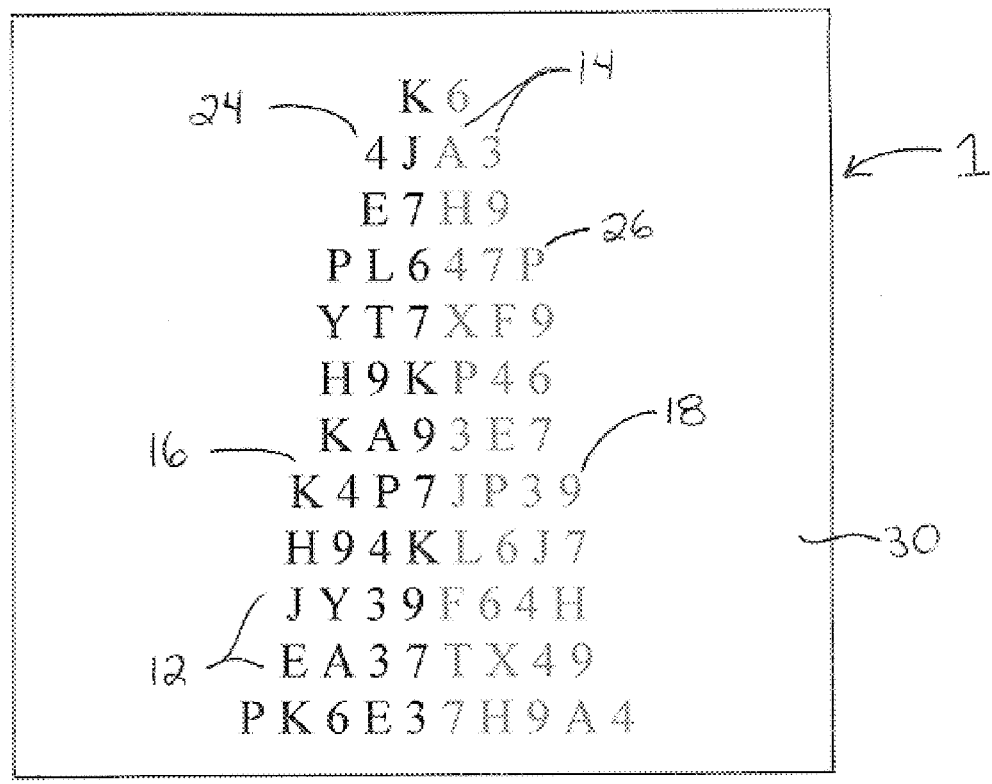
FIG. 1 is a chart of the present invention having lines of letters and numerals with a first color, and letters and numerals of a second color.

FIG. 1 illustrates an eye chart 1 that can be used in determining visual acuity. The eye chart 1 has a plurality of lines 12 with symbols 14. The symbols 14 used in the lines 12 are chosen from a set of symbols. The set of symbols 14 include letters 16 and numerals 18. Each line 12 has a mix of letters 16 and numerals 18.

The letters 16 are block letters in upper case. In the embodiment illustrated, the letters 16 and the numerals 18 in a given line 12 are substantially equally in size. In an alternative embodiment, the letters 16 and the numerals 18 in each line 12 decrease in size with each successive line, as shown more clearly in and discussed in detail with regard to FIG. 2.

Each symbol in the set of symbols has distinguishable features from other symbols in the set. The distinguishable feature of the symbol enables one having visual acuity of 20/20 to consistently determine each symbol when reading the symbol at a distance of 20 feet and when the symbol is designed to be read at 20 feet. Each symbol is formed by strokes, and is distinguished from other symbols in the set by having at least one distinct stroke when compared with other symbols in the set. The distinct stroke subtends greater than 1 minute arc in width, so that the stroke renders each symbol in the set distinguishable from other symbols in the set, even at a distance. Accordingly, the symbols in the set are substantially equally legible and recognizable.

Each symbol in the set is chosen so as not to be easily confused with another similar looking symbol. Symbols that are confusingly and strikingly similar have been excluded from the set to aid in the elimination of potential subjective recording of visual acuity. Consistent quantification of visual acuity may be attained utilizing charts with the distinct letters 16 and numerals 18. The consistent quantification aids in monitoring, as well as diagnosing, neurological disorders.

The following numerals are included in the set of symbols: 3, 4, 6, 7, and 9. The following letters are included in the set of symbols: A, E, F, H, J, K, L, P, T, X, and Y. Because the following groups of letters and numerals closely resemble each other, they are excluded from the set of symbols: 1 and I; 5, S, B and 8; 0, D and O; C, G and Q; M and N; R and P; U, V and W; and 2 and Z.

Figure 2:
FIG. 2 is a chart having lines with symbols of letters, numerals and pictorial objects.

FIG. 2 illustrates an embodiment of an eye chart 10 having lines 12 with symbols 14 of letters 16, numerals 18 and pictorial objects 20. In the embodiment shown, the letters and numerals are from the set of symbols described with regard to FIG. 1. In an alternative embodiment, the letters 16 and numerals 18 in the chart are chosen from a set that includes all 10 numerals, and all 26 letters of the alphabet. The pictorial objects 20 have distinct, non-confusing shapes. The objects 20 in FIG. 20 are illustrative of the types of distinct shapes in the eye chart of the present invention, and are not limited to these shapes.

The font sizes of each of the lines 12 in the chart 10 of FIG. 2 are based on Standard Snellen sizes used in a Snellen chart. As the lines 12 (or rows) progress down the chart, the font size decreases. A Snellen fraction is the value associated with a particular line in the chart. The Snellen fraction is defined as: visual acuity=(distance at which the letter is read)/(distance at which it should normally be read). The font size on a top row of the Snellen chart may start with a Snellen fraction of 20/200 or 20/160, and progressively decline in font size for successive rows, such as 20/125, 20/100, down to 20/20.

In another embodiment, the symbols logarithmically decrease in size down the chart. In yet another embodiment, the symbols have sizes that correspond to Jaeger sizes.

In one embodiment, the eye charts are on reading cards. The symbols in the reading cards are in at least one of Snellen sizes or Jaeger sizes.

In another embodiment, the letters 16 used in the chart 1, 10 are letters of foreign alphabets. For instance, letters from Russian, Hebrew, Greek, and Arabic are used in the chart. Letters that are not easily distinguishable from other symbols in the set are excluded to aid in eliminating potential subjective recordation of the valuation for visual acuity.

For instance, from the Russian alphabet, numerals 3 and 6, and the following characters are excluded from the set of symbols:

Ц,Ш,Щ,ы,в,Ьь,М,С,Л,З,Ъ,,О,Ж,Ю,Ч,Х,Э

From the Russian alphabet, the following characters are included in the set of symbols:

У,К,Е,Н,Г,Ф,А,П,Р,Я,Т,И

From the Hebrew alphabet, the following characters are excluded from the set of symbols:

ט, ג, ח, מ, ז, ח, ב, ס, ת, י, ד, ], ף, ו, כ, ם, ], ו,

From the Hebrew alphabet, the following characters are included in the set of symbols:

צ, ל, ע, ש, פ, א, ר,

From the Greek alphabet, the following characters are excluded from the set of symbols:

Θ,Ι,Ο,Σ,Ε,Δ,Λ,Ψ,Φ,Β,Ν,Μ

From the Greek alphabet, the following characters are included in the set of symbols:

Α, Γ,Ζ,ζ,Η,Κ,Ξ,Π,Ρ,Τ,Υ,Χ,Ω

After the person has identified the symbols 14 in a given line 12 on the eye chart 1, 10 accurately, a value associated with that line 12 is recorded by a doctor. If the patient reads a given line 12 accurately, the doctor directs the patient to read a line 12 that has a smaller font. If the patient is unable to read the symbols in that line accurately, the doctor records a value corresponding with the previously read line. If the patient is able to read the numerals, but not the letters in the line, the doctor records a first value associated with the acuity with regard to numerals, and records a second value associated with the acuity with regard to letters. These two values may be compared with each other, as discussed in more detail below. The patient is scored for each eye.

The eye charts of FIGS. 1 and 2 aid in testing, monitoring and diagnosing neurological diseases and disorders, in particular, Alzheimer's, by comparison of the recorded values. In addition, the eye charts aid in assessing clinical treatments, monitoring of the reaction of a patient to drugs and progress of clinical treatments, as well as aid in research of different ophthalmological and neurological diseases and disorders. The eye charts aid in this by consistently accurately measuring visual acuity and by enabling distinction between different levels of mental perception.

The ability to identify numerals 18 in the eye charts 1, 10 more accurately than letters 16 can be an indication of a neurological disease, because numerals typically require less abstract thought than letters. The recorded value associated with the visual acuity with regard to numerals in the chart acts as the control data. When the recorded value associated with letters is worse than that of the numerals, a neurological disease or disorder, such as Alzheimer's, may be suspected. Further testing and diagnosis of the patient are likely to be undertaken, but utilization of the eye chart with the different types of symbols is a quick and cost efficient method for making a preliminary screening.

Use of the distinct symbols aids in the assessment of the neurological disease because the values that are recorded minimize potential error. The values are consistent for similar circumstances, and there is minimal room for subjectivity in evaluation of the appropriate values. Accordingly, when the values for letters and numerals are very close, there is a less likelihood of a neurological disease. And when the values for letters and numerals are far apart, there is a greater likelihood of a neurological disease.

In addition, the ability to identify pictorial objects in the eye charts more accurately than numerals and/or letters can also be a sign of a neurological disease, because pictorial objects typically require less abstract thought than numerals and/or letters. From the chart in FIG. 2, a value associated with an accuracy of identification of the pictorial object on the eye chart is recorded. This value is compared with the values associated with the accuracy of identification of the letters and the numerals. If the value associated with visual acuity is less for pictorial objects than for numerals and letters, this may be an indication of a neurological disease or disorder.

In one embodiment, symbols 14 in the lines 12 of the eye charts have different colors, as illustrated in FIG. 1. The symbols in the charts may be any color or combination of colors. For instance, in FIG. 1, half of the symbols 14 in each line 12 are colored black and the other half are colored red. Some of the numerals 18 are red and some are black, and some of the letters 16 are red and some are black. In one embodiment, the red and black symbols are randomly spread throughout the eye chart (See FIG. 3).

In the same method as described above, the doctor records the accuracy of identification of the red symbols and of the black symbols of FIG. 1. Color perception, more particularly red saturation, declines more rapidly than visual acuity in some optic nerve diseases, such as Multiple Sclerosis. By comparing recorded values of visual acuity of black symbols with that of, say, red symbols, one can determine if red perception has declined. For a normal retina, there is a higher acuity associated with red as compared with black. When the recorded acuity value associated with the red symbols is no better than that of the black symbols, a neurological disease or disorder, such as Multiple Sclerosis, may be suspected. The more drastic the difference between the recorded values of the red and black symbols, the more the decline in red perception.

In addition to determining decline of color perception, quantification of that decline is enabled through use of the eye chart of FIG. 1. A patient's progress with regard to color perception is monitored over time by comparing the accuracy of the identification of the black symbols (standard visual acuity) with the accuracy of the identification of the red symbols (red visual acuity) for a given test. Previous test results may be compared with present test results to monitor progress. Therefore, using the chart illustrated in FIG. 1, not only tests for neurological diseases, such as Alzheimer's, by comparing the accuracies of identification between the letters and numerals, but also tests for loss of color vision by comparing the accuracies of identification between differently colored symbols.

In another embodiment, the symbols 14 in the eye chart that are colored red or black are not distinct symbols (not shown). For instance, there may be a red "B", a black "1", and a red "M" in a given line 12 on the chart. In one embodiment, the pictorial objects as shown in FIG. 2 may be in a single color or various colors other than black.

Figure 3:
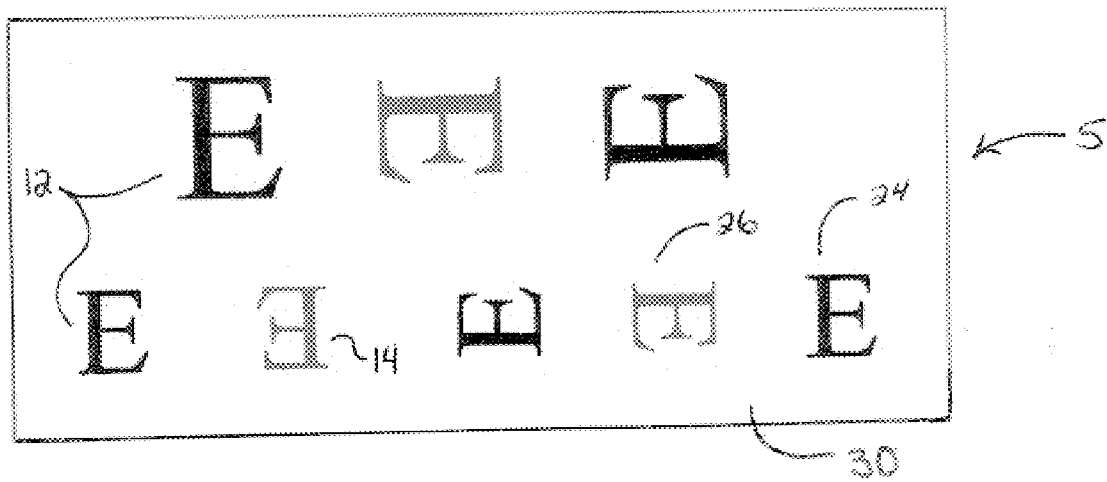
FIG. 3 is a Tumbling E chart with some symbols having a first color, and other symbols having a second color.

FIG. 3 illustrates an eye chart 5 with lines 12 having symbols 14, including a first symbol 24 in a first color, and a second symbol 26 in a second color. The first and second symbols are substantially equal in size and distinguishing features, so that each symbol is substantially equally legible. In the present invention, the first symbol 24 is black and the second symbol 26 is red. The symbols 14 in the eye chart 5 are the letter "E" in various orientations.

Using a tumbling E chart, or a matching test, such as is done with the HOTV chart, pictorial objects or blocks, with different colored symbols enables quantification of change in color perception. These charts are particularly useful to monitor color perception changes in people who have had strokes, children, aphasic adults and illiterates. A value associated with an accuracy of identification of each of the first colored symbol and the second colored symbol on the eye chart are recorded. The values are then compared to each other as described above.

A background 30 in the eye charts 1, 5, 10 is white. However, in one embodiment, the symbol color and background color may be reversed, so that the symbols are white, while the background is black (not shown). In another embodiment, the background of the eye chart is dark gray. A dark gray background stresses the ability to see red and is particularly useful with red symbols. A patient with normal vision viewing an eye chart on a dark gray background typically sees red symbols better than black symbols. However, a patient with advanced red desaturation, viewing the same eye chart, typically sees the red symbols with the same visual acuity as the black symbols.

Figure 4:
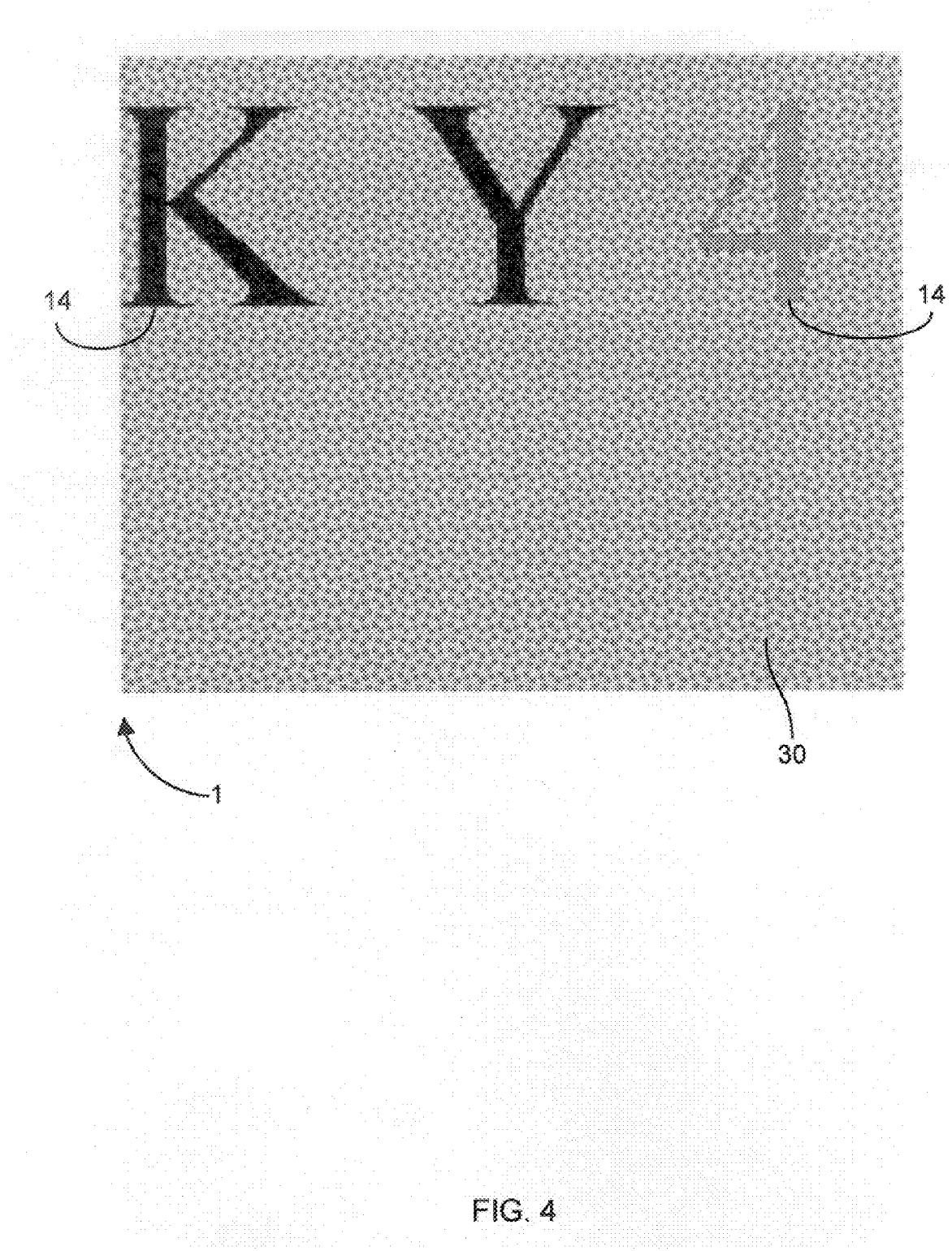
FIG. 4 is a chart having colored symbols on a colored and patterned background.

In yet other embodiments such as that shown in FIG. 4, the chart 1 has the distinct symbols 14 over a colored and patterned background 30 of a red and yellow pattern. In this example, the letters "K" and "Y" are black while the numeral "4" is green. For some charts, backgrounds of pale yellow or bright red may be useful. In testing of color blindness, background colors such as red-purple and gray dots, and red-yellow dots, are useful. Such background colors are the standard colors of the Ishihara plates. For instance, a green-dotted numeral 9 and a blue-green-dotted 3 may be set among red and red-purple dots or red and gray dots. One with a particular type of color blindness, sees both blue green and red as gray. Accordingly, he cannot see the 3 but can see the 9, which appears to be light yellow. One with another type of color blindness cannot see the 9 but can see the 3 which appears slightly bluer than the other dots, which appear gray.

As a result of the colored backgrounds, not only is the patient tested for color blindness, but also the patient is monitored for progressive diseases that affect color vision. Some prescription drugs, such as digoxin, cause color distortions for a patient when the blood level is too high. An eye chart with a colored background can be used to monitor the blood level without conducting a blood test. As the blood level increases to toxic levels, the color visual acuity for a chart constructed for the particular drug should decrease. For example, since digoxin causes yellow vision, comparison of vision on an acuity chart with a white background may be better than the acuity with a yellow background. Also, the progress of retinal dystrophies may be monitored in a similar same way, without conducting electroretinograms. Any of the charts or variations described above may have a white, a colored or a patterned background.

While various embodiments of this invention have been shown and described, it would be apparent to those skilled in the art that many more modifications are possible without departing from the inventive concept herein. For example, the term "chart" not only refers to a distance chart, but also the term includes far charts, near charts, hand held charts, such as cards. The cards may be paper or plastic, and are generally used in the HOTV matching test. "Charts" also refers to electronic charts, film charts, transparency charts, and projections, including one row of symbols at a time.

It is, therefore, to be understood that within the scope of the appended claims, this invention may be practiced otherwise than as specifically described.

What is claimed is:

1. An eye chart for testing the visual acuity of a patient, the eye chart comprising a plurality of symbols, the symbols arranged in a plurality of lines, each line representing a particular visual acuity, wherein the symbols are selected from a set of symbols consisting essentially of the characters A, E, F, H, J, K, L, P, T, X, and Y and the numerals 3, 4, 6, 7, and 9.

2. The eye chart of claim 1 wherein the symbols consist essentially of a plurality of characters selected from the set of symbols.

3. The eye chart of claim 1 wherein the symbols consist essentially of a plurality of numerals selected from the set of symbols.

4. The eye chart of claim 1 wherein at least one symbol is of the color black and at least one symbol is of a color selected from the group consisting of red and green.

5. The eye chart of claim 1 wherein the symbols are divided into first and second subsets of symbols.

6. The eye chart of claim 5 wherein the first subset of symbols consists essentially of a plurality of characters selected from the set of symbols and the second subset of symbols consists essentially of a plurality of numerals selected from the set of symbols.

7. A method for testing the visual acuity of a patient using the eye chart of claim 5, the method comprising the steps of:
   recording a first value representing the accuracy with which the patient is able to accurately identify the symbols from the first subset of symbols;
   recording a second value representing the accuracy with which the patient is able to accurately identify the symbols from the second subset of symbols; and
   comparing the first and second values.

8. The method of claim 7 wherein the first subset of symbols are of a first color and the second subset of symbols are of a second color.

9. The method of claim 7 wherein the first subset of symbols consists essentially of a plurality of numerals selected from the set of symbols and the second subset of symbols consists essentially of a plurality of characters selected from the set of symbols.

10. The eye chart of claim 1 further comprising a background.

11. The eye chart of claim 10 wherein the background is a color selected from the group consisting of white, black and gray.

12. The eye chart of claim 10 wherein the background comprises a plurality of dots, each dot having a color, the colors selected from the group consisting of red, purple, gray, yellow, and combinations thereof.

13. An eye chart for testing the visual acuity of a patient, the eye chart comprising a plurality of symbols, the symbols arranged in a plurality of lines, each line representing a particular visual acuity, wherein each symbol is defined by a plurality of strokes, and each symbol is distinguishable from each other symbol by having at least two strokes distinct from the strokes defining each other symbol.

14. The eye chart of claim 13 wherein each stroke subtends greater than 1 minute arc in width.

15. The eye chart of claim 13 wherein each symbol comprises a pictorial object.

16. The eye chart of claim 15 wherein each symbol comprises a character from an alphabet.

17. The eye chart of claim 15 wherein each symbol comprises a numeral.

18. A method for testing the visual acuity of a patient comprising the steps of:
   providing an eye chart comprising a plurality of symbols, the symbols arranged in a plurality of lines, each line representing a particular visual acuity, wherein the symbols are selected from a set of symbols consisting essentially of the characters A, E, F, H, J, K, L, P, T, X, and Y and the numerals 3, 4, 6, 7, and 9; and
   recording a value representing the accuracy with which the patient is able to accurately identify the symbols from at least one of the plurality of lines.

19. The method of claim 18 wherein the line is a first line and the value is a first value, the method further comprising the step of recording a second value representing the accuracy with which the patient is able to accurately identify the symbols from a second of the plurality of lines.

20. A method for testing a patient for a neurological disorder comprising the steps of:
   providing an eye chart comprising a plurality of characters from an alphabet and a plurality of numerals, the characters and numerals arranged in a plurality of lines, each line representing a particular visual acuity;
   recording a first value representing the accuracy with which the patient is able to accurately identify the characters from at least one of the plurality of lines;
   recording a second value representing the accuracy with which the patient is able to accurately identify the numerals from at least one of the plurality of lines; and
   comparing the first and second values.

21. The method of claim 20 further comprising the steps of repeating the steps in order to obtain first and second test results and comparing the first and second test results.

22. The method of claim 21 wherein the second test results are obtained at least one month after the first test results are obtained.

23. A method for testing a patient for perception of the color red comprising the steps of:
   providing an eye chart comprising a plurality of red symbols and a plurality of non-red symbols, the symbols arranged in a plurality of lines, each line representing a particular visual acuity;
   recording a first value representing the accuracy with which the patient is able to accurately identify the red symbols from at least one of the plurality of lines;
   recording a second value representing the accuracy with which the patient is able to accurately identify the non-red symbols numerals from at least one of the plurality of lines; and
   comparing the first and second values.

24. The method of claim 23 wherein the non-red color is selected from black and green.

* * * * *